United States Patent [19]

Inoue et al.

[11] Patent Number: 4,784,792

[45] Date of Patent: Nov. 15, 1988

[54] FERROELECTRIC PYRIDINE COMPOUND AND LIQUID CRYSTAL COMPOSITION

[75] Inventors: Hiromichi Inoue; Takashi Inukai; Kouji Ohno; Kazutoshi Miyazawa; Shinichi Saito, all of Kanagawa, Japan

[73] Assignee: Chisso Corporation, Ohsaka, Japan

[21] Appl. No.: 942,626

[22] Filed: Dec. 16, 1986

[30] Foreign Application Priority Data

Dec. 27, 1985 [JP] Japan ................... 60-293934

[51] Int. Cl.⁴ ............ G02F 1/13; G09K 19/34; C07D 211/70
[52] U.S. Cl. ............ 252/299.61; 252/299.01; 252/299.5; 350/350 S; 546/339
[58] Field of Search ........ 252/299.5, 299.61, 299.01; 350/350 S; 546/339

[56] References Cited

U.S. PATENT DOCUMENTS

| | | | |
|---|---|---|---|
| 4,657,695 | 4/1987 | Saito et al. | 252/299.61 |
| 4,684,220 | 8/1987 | Shionozaki et al. | 252/299.61 |

FOREIGN PATENT DOCUMENTS

| | | | |
|---|---|---|---|
| 149238 | 7/1985 | European Pat. Off. | 252/299.61 |
| 194153 | 9/1986 | European Pat. Off. | 252/299.61 |
| 3515373 | 11/1986 | Fed. Rep. of Germany | 252/299.61 |
| 61-24571 | 2/1986 | Japan | 252/299.61 |
| 61-91284 | 5/1986 | Japan | 252/255.61 |
| 2092169 | 8/1982 | United Kingdom | 252/299.61 |
| 2161808 | 1/1986 | United Kingdom | 252/299.61 |

| | | | |
|---|---|---|---|
| 8600087 | 1/1986 | World Int. Prop. O. | 252/299.61 |
| 8606401 | 11/1986 | World Int. Prop. O. | 252/299.61 |

OTHER PUBLICATIONS

Pavluchenko, A. I. et al., Advances in Liquid Crystal Research and Applications, Bata, L., Ed., Pergamon Press, Oxford, pp. 1007–1013 (1980), C.A., vol. 104, 129767a (1986).

Gray, G. W. et al., Liquid Crystals & Plastic Crystals, vol. 1, John Wiley & Sons, Inc., pp. 137–143 (1974).

Primary Examiner—Teddy S. Gron
Attorney, Agent, or Firm—Wenderoth, Lind & Ponack

[57] ABSTRACT

A ferroelectric pyridine compound suitable as a liquid crystal for display mode utilizing ferroelectric properties and exhibiting SC* phase at a temperature somewhat higher than room temperature and a liquid crystal composition are provided, which compound is expressed by the formula

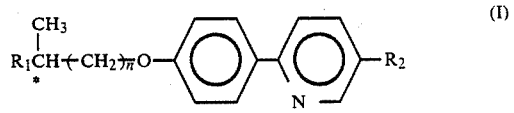

(I)

wherein n represents an integer of 0 to 8, $R_1$ represents an alkyl group of 2 to 18 carbon atoms, $R_2$ represents an alkyl group of 1 to 18 carbon atoms and the symbol * indicates that C having the symbol attached thereon is an optically active carbon atom.

8 Claims, No Drawings

FERROELECTRIC PYRIDINE COMPOUND AND LIQUID CRYSTAL COMPOSITION

BACKGROUND OF THE INVENTION

1. Field of the Invention

This invention relates to a novel liquid crystal substance and a liquid crystal composition containing the liquid crystal substance, and more particularly it relates to a chiral liquid crystal substance having an optically active group and a chiral liquid crystal composition containing the same.

2. Description of the Related Art

At present, as liquid crystal display elements, the TN (Twisted Nematic) type display mode has been most broadly employed, but it is inferior to emissive type display elements such as those of electroluminescence, plasma display, etc. in the aspect of response speed. Thus, various improvements in this respect have been attempted, but nevertheless it does not seem that a possibility of improvement to a large exent has been achieved. Accordingly, various liquid crystal display devices based upon another principle in place of that of the TN type display elements have been attempted. As one of these devices, there is a device according to a display mode utilizing ferroelectric liquid crystals (N. A. Clark et al, Applied Phys. lett., 36,899 (1980)).

This mode utilizes the chiral smectic C phase (hereinafter abbreviated to SC* phase) or chiral smectic H phase (hereinafter abbreviated to SH* phase), and the temperature range exhibiting these phases is preferred to be in the vicinity of room temperature.

Mainly in order to develop liquid crystal substances suitable for being utilized for this display mode, the present inventors have searched for various liquid crystal substances having an optically active group and as a result have achieved the present invention.

SUMMARY OF THE INVENTION

The present invention resides in a ferroelectric pyridine compound expressed by the formula

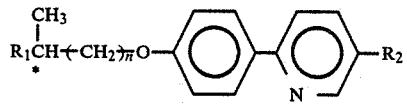

(I)

wherein n represents an integer of 0 to 8, $R_1$ represents an alkyl group of 2 to 18 carbon atoms, $R_2$ represents an alkyl group of 1 to 18 carbon atoms and the symbol * indicates that the C having the symbol attached thereon is an optically active carbon atom, and a liquid crystal composition containing at least one of the compounds as a component.

DETAILED DESCRIPTION OF PREFERRED EMBODIMENTS

The phase transition points of representative examples of the compounds of the formula (I) of the present invention are shown in Table 1.

In the column of the phase transition points in Table 1, C represents crystalline phase; SH*, chiral smectic H phase; SG*, chiral smectic G phase; SF*, chiral smectic F phase; SA, smectic A phase; Ch, cholosteric phase; and I, transparent phase, and the symbol · indicates that the respective phases are exhibited, while the symbol — indicates that the respective phases are not exhibited. Further, the numeral on the right side of a symbol · indicates the phase transition point from the phase corresponding to the symbol · to the phase corresponding to a symbol · closest to the numeral.

Most of the compounds expressed by the formula (I) exhibit SC* phase suitable to the display mode utilizing the ferroelectric properties at a somewhat higher temperature than room temperature. Particularly the temperature ranges of the compounds of sample No. 4, etc. are 20° C. or higher and moreover the melting point of sample No. 4 is as low as 12.5° C. and also, ferroelectric properties are exhibited in the liquid phases starting from its melting point up to the SC* phase. Further, the values of the spontaneous polarization are large. In the case of the compound of sample No. 4, the value is as large as about 4 $nC/cm^2$ at 38° C. (SC* phase) in spite of its asymmetric carbon atom being apart from the central part of the molecule.

TABLE 1

| Sample No. | In Formula (I) $R_1$ | n | $R_2$ | C | SH* | SG* | SF* | SC* | SA | Ch | I | Note |
|---|---|---|---|---|---|---|---|---|---|---|---|---|
| 1 | $C_2H_5$ | 5 | $C_6H_{13}$ | . 45.2 | (. 44.2) | . 48.5 | . 53.8 | . 63.0 | — | — | . | |
| 2 | $C_6H_{13}$ | 0 | $C_7H_{15}$ | . 18.5 | — | — | — | — | — | — | . | |
| 3 | $C_2H_5$ | 2 | $C_7H_{15}$ | . 41.7 | — | — | — | . 43.0 | — | — | . | |
| 4 | $C_2H_5$ | 4 | $C_7H_{15}$ | . 12.5 | — | . 23.2 | . 37.5 | . 58.4 | — | — | . | Example 1 |
| 5 | $C_8H_{17}$ | 1 | $C_7H_{15}$ | . 33.5 | — | — | — | — | (. 29.4) | — | . | |
| 6 | $C_2H_5$ | 3 | $C_8H_{17}$ | . 30.5 | — | . 34.8 | . 51.0 | . 62.7 | — | — | . | |
| 7 | $C_2H_5$ | 4 | $C_8H_{17}$ | . 21.5 | — | (. 9.7) | . 38.5 | . 59.1 | — | — | . | |
| 8 | $C_2H_5$ | 5 | $C_8H_{17}$ | . 34.4 | — | (. 28.5) | . 56.2 | . 70.5 | — | — | . | |
| 9 | $C_2H_5$ | 3 | $C_9H_{19}$ | . 41.3 | — | — | . 53.3 | . 64.8 | — | — | . | |
| 10 | $C_2H_5$ | 4 | $C_9H_{19}$ | . 35.5 | — | — | . 45.4 | . 63.0 | — | — | . | |
| 11 | $C_2H_5$ | 1 | $C_{10}H_{21}$ | . 35.0 | — | — | . 48.1 | . 49.8 | . 54.2 | — | . | |
| 12 | $C_2H_5$ | 3 | $C_{10}H_{21}$ | . 35.5 | — | — | . 53.0 | . 64.0 | — | — | . | |

In addition, compounds wherein the optically active group on the left side of the formula (I) of the present invention is a linear chain alkyl i.e.

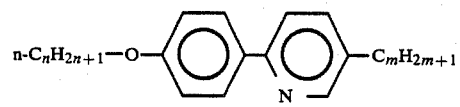

(A)

wherein n represents an integer of 1 to 7 and m is 4 or 6, are known (A. I. Pavulchenko et al; Advances in Liquid orystal Research and Applications; Pergamon Press, 1980, p1007), but most of the compounds exhibit only SA phase, and only those wherein n=5 and m=6 have been assumed to exhibit SA phase and SC phase, but at any rate, no SC* phase exhibiting ferroelectric properties are exhibited.

Since the compounds of the formula (I) of the present invention have a superior compatibility with other compounds such as those exhibiting SC* phase, SH* phase, those exhibiting cholesteric phase, etc., it is possible to broaden the temperature range of the SC* phase by blending them with the above other compounds.

In the case where a chiral smectic liquid crystal composition is constituted, it is possible to constitute it only from a plurality of the compounds of the formula (I), and it is also possible to blend the compounds of the formula (I) with other chiral smectic liquid crystals or achiral smectic liquid crystals and thereby prepare a liquid crystal composition exhibiting SC* phase.

In the case where the light-switching effect of SC* phase is applied to display elements, there are three superior specific features as compared with TN display mode. The first specific feature is that the response is very fast, that is, the response time is 1/100 or less of that in the case of elements of TN display mode. The second specific feature is that there is a memory effect so that multiplex drive is easy in cooperation with the above high-speed response properties. The third specific feature is as follows; In order to obtain a gray scale according to TN display mode, this is carried out by controlling the impressed voltage, but there are difficult problems of the temperature-dependency of the threshold voltage, the voltage-dependency of the response speed, etc., whereas in the case where the light switching effect of SC* phase is applied, it is possible to easily obtain the gray scale by controlling the polarity inversion time; hence the above case is very suitable to graphic display.

As the display method, two modes are considered, that is, one method is of a birefringence type using two sheets of polarizers, and another is of guest-host type using dichroic dyestuffs. Since SC* phase has a spontaneous polarization, the molecule is inverted around the helical axis as a rotating axis by inverting the polarity of an impressed voltage. A liquid crystal composition having SC* phase is filled into a liquid crystal cell subjected to aligning treatment so that the liquid crystal molecules can be aligned in parallel to the electrode surfaces, and the resulting cell is placed between two sheets of polarizers arranged so that a director for the liquid crystal molecules and a polarizing plate opposed thereto, followed by impressing a voltage to invert the polarity, whereby a bright field of vision and a dark field of vision (determined by the opposite angle of the polarizers) are obtained.

On the other hand, in the case of operation according to the guest-host type, it is possible to obtain a bright field of vision and a colored field of vision (determined by the arrangement of the polarizing plate) by inverting the polarity of the impressed voltage.

In general, it is difficult to align the liquid crystal molecules in the smectic state in parallel to the glass vall surface, thus, the liquid crystal molecules have been aligned by cooling them very slowly (at a rate of 1° to 2° C./hr) starting from the isotropic liquid thereof in a magnetic field of several tens killogauss or more. However, in the case of a liquid crystal substance having cholesteric phase in the range of temperatures higher than those at which smectic phase is exhibited, when cooling is carried out starting from the temperatures at which cholesteric phase is exhibited, down to those at which smectic phase is exhibited, at a cooling rate of 1° C./min. while a direct current voltage of 50 to 100 V is impressed in place of the magnetic field, it is possible to easily obtain a uniformly aligned monodomain state.

In addition, as to racemic substances corresponding to the compounds of the formula (I), when an optically active alcohol used as a raw material in the preparation of the optically active substance (I) shown below is replaced by the corresponding racemic alcohol, the racemic substances are similarly prepared and exhibit almost the same phase transition points as those of the compounds of the formula (I).

Since the compounds of the formula (I) also have an optically active carbon atom, they have a capability of inducing a twisted structure when they are added to nematic liquid crystals. Nematic liquid crystals having a twisted structure, i.e., chiral nematic liquid crystals do not form the so-called reverse domain (dechiralization lines) of TN type display elements; hence it is possible to use the compounds of the formula (I) as an agent for preventing the formation of the reverse domain.

Next, the process for preparing the compounds of the formula (I) will be described. The compounds of the formula (I) may be prepared through the following passageways;

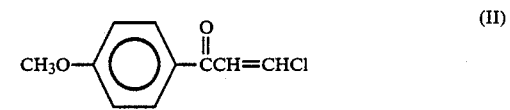

(II)

(1st step)

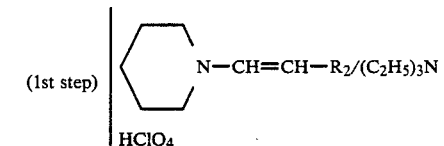

(III)

(2nd step) CH$_3$COONH$_4$/CH$_3$COOH

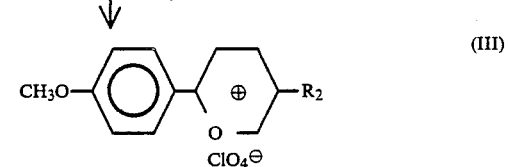

(IV)

(3rd step) HBr/CH$_3$COOH

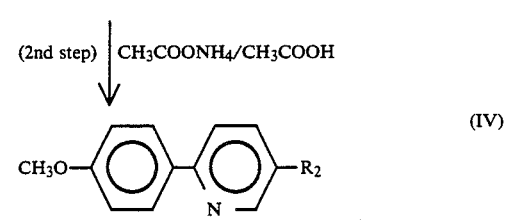

(V)

(4th step)

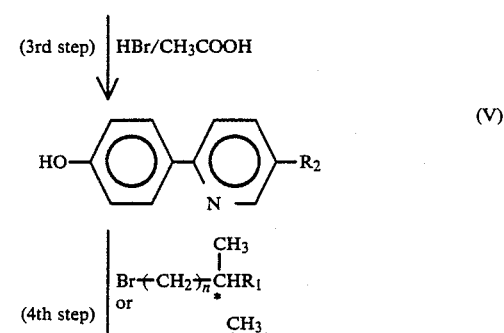

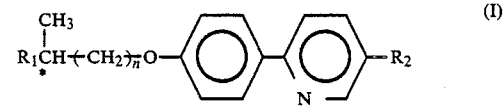

(I)

Namely, p-methoxyphenyl-β-chlorovinyl ketone (II) as a known substance is reacted with an ethylamine in the presence of in a solvent and further reacted with perchloric acid to obtain a pyrilium salt (III), which is then reacted with ammonium acetate in a solvent, preferably acetic acid, to obtain a compound (IV), which is then reacted with hydrobromic acid in a solvent, preferably acetic acid, to obtain a compound (V), which is then heated together with an optically active alkylbromide (or an optically active alkyl tosylate) and potassium hydroxide in a solvent, preferably ethanol, to obtain an objective compound of the formula (I).

The ferroelectric pyridine compounds of the present invention will be described in more detail by way of Examples.

EXAMPLE 1

Preparation of optically active 2-[p-(5-methylheptyloxy)phenyl]-5-heptylpyridine (a compound of the formula (I) wherein $R_1=C_2H_5$, $R_2=C_7H_{15}$ and n=4) (sample No. 4)

(The first step)

N-heptenylpiperidine (41.8 g, 0.20 mol) and triethylamine (20 g, 0.20 mol) were dissolved in ethyl ether (100 ml) with stirring, followed by dropwise adding to the resulting solution, a solution of the above compound (II) (30 g, 0.20 mol) prepared in advance according to a known method, dissolved in ethyl ether (200 ml) while keeping the temperature of the system at 35° C. or lower, agitating the resulting mixture at room temperature for 8 hours, adding water (100 ml) and toluene (50 ml), transferring the mixture into a separatory funnel, twice washing the resulting organic layer with water, distilling off the solvent under reduced pressure, adding 70% perchloric acid (100 ml) to the residue, adding water (100 ml), heating the mixture under reflux for 10 minutes, cooling the resulting material, washing the resulting crystals with ethyl ether and drying the crystals to obtain 5-heptyl-2-(p-methoxyphenylpyrilium) perchlorate (compound (III), $R=C_7H_{15}$) (48.0 g).

(The second step)

5-Heptyl-2-(p-methoxyphenylpyrilium) perchlorate obtained in the above first step (48.0 g, 0.125 mol) was heated under reflux with stirring together with ammonium acetate (96 g, 1.25 mol) and acetic acid (500 ml) for 4 hours, followed by pouring the reaction fluid into water, dissolving the resulting crystals in toluene, transferring the resulting solution into a separatory funnel, three times washing with water, distilling off the solvent under reduced pressure and recrystallizing the residue to obtain 5-heptyl-2-(p-methoxyphenyl) pyridine (compound (IV), $R=C_7H_{15}$) (20 g) having a melting point of 54.4°–56.5° C.

In addition, compounds of the formula (IV) wherein $R_2=C_8H_{17}$, $C_9H_{19}$ or $C_{10}H_{21}$ had melting points of 60.7°–62.2° C., 55.0°–57.4° C. or 61.1°–62.9° C., respectively.

(The third step)

5-Heptyl-2-(p-methoxyphenyl) pyridine obtained in the above second step (20 g, 0.071 mol), hydrobromic acid (47%, 130 ml) and acetic acid (300 ml) were heated under reflux for 30 hours, followed by cooling the mixture, pouring it in water, filtering off the resulting crystals, dissolving the crystals in 2N NaOH aqueous solution, further adding acetic acid to make the solution acidic, filtering off the resulting crystals and recrystallizing them to obtain 5-heptyl-2-(p-hydroxyphenyl) pyridine (compound (V), $R=C_7H_{15}$) (13 g) having a melting point of 105.2°–105.9° C.

In addition, compounds of the formula (V) wherein $R=C_6H_{13}$, $C_8H_{17}$, $C_9H_{19}$ or $C_{10}H_{21}$ had melting points of 117.6°–118.0° C., 93.2°–95.0° C., 85.0°–87.5° C. or 90.4°–91.8° C., respectively.

(The fourth step)

5-Heptyl-2-(4-hydroxyphenyl) pyridine (10 g, 0.037 mol) obtained in the above third step, ethanol (100 ml), pottasium hydroxide (3.0 g, 0.045 mol) and optically active 5-methylheptylbromide (9 g, 0.045 mol) were heated under reflux with stirring for 4 hours, followed by cooling the mixture, adding water and toluene, transferring the mixture into a separatory funnel, washing the resulting organic layer with 2N-NaOH aqueous solution, washing it with water, distilling off the solvent under reduced pressure and recrystallizing the residue in a freezer to obtain the objective optically active 2-(5-methylheptyloxyphenyl)-5-heptylpyridine (I)(6.5 g).

The phase transition points of this product were as follows:

C-SG* point: 12.5° C., SG*-SF* point: 23.2° C., SF*-SC* point: 37.5° C. and SC*-I point: 58.4° C.

Further, its elemental analysis values accorded well with its calculated values as follows:

|   | Observed values (%) | Calculated values (in terms of $C_{26}H_{39}NO$) |
|---|---|---|
| C | 81.21 | 81.84 |
| H | 10.1 | 10.30 |
| N | 3.40 | 3.67 |

By replacing N-heptenylpiperidine used in the first step by other N-alkenylpiperidines and replacing optically active 5-methylheptyl bromide of the fourth step by various kinds of optically active alkylbromides or optically active alkyl tosylates, other compounds of the formula (I) were obtained in the same manner as the above.

The phase transition points of these compounds are shown in Table 1 together with those of Example 1.

In addition, a racemic substance corresponding to the compound of sample No. 6 was prepared and its phase transition points were measured. The points were as follows:

C $\xrightarrow{30.8° C.}$ SG $\xrightarrow{33.8° C.}$ SF $\xrightarrow{51.0° C.}$ SC $\xrightarrow{62.7° C.}$ I.

Namely, its phase transition points accorded almost with those of sample No. 6 except that it exhibited achiral phases.

EXAMPLE 2 (COMPOSITION 1)

A nematic liquid crystal composition consisting of

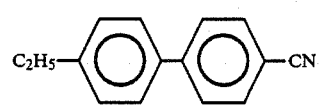

20 wt. %

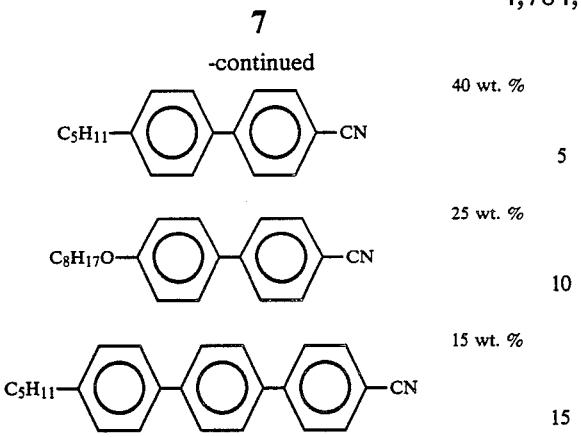 40 wt. %

25 wt. %

15 wt. % was filled into a cell having transparent electrodes provided with polyvinyl alcohol (PVA) applied thereonto, followed by rubbing the resulting surfaces to subject the resulting surfaces to parallel aligning treatment and having a distance between the electrodes of 10 μm to prepare a TN type cell, which was then observed under a polarizing microscope, as a result, formation of a reverse twist domain was observed.

To the above nematic liquid crystal composition added a compound of the formula (I) of the present invention wherein $R_1=C_8H_{17}$, $n=1$ and $R_2=C_7H_{15}$ i.e.

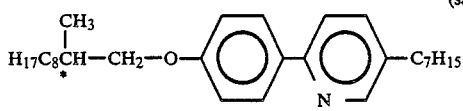 (sample No. 5)

in a quantity of 1% by weight and a TN type cell prepared in the same manner as above was similarly observed. As a result, the above reverse twist domain was dissolved and a uniform nematic phase was observed.

EXAMPLE 3 (COMPOSITION 2)

Using the above sample No. 3 of the present invention and another SC* compound, the following equimolecular composition was prepared:

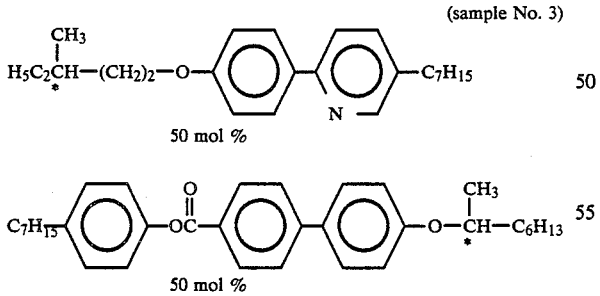

(sample No. 3)

50 mol %

50 mol %

The composition was filled in a cell 2 μm thick provided with transparent electrodes having PVA applied thereonto, followed by rubbing the resulting surfaces to subject the resulting surfaces to parallel aligning treatment, and the resulting liquid crystal cell was provided between two sheets of crossed polarizers, followed by impressing an electric field thereto.

Impressing 20 V, change in the intensity of transmitted light was observed. The response time was sought from the change in the intensity of transmitted light at that time to give about 70 μsec at 25° C.

In addition, with the above composition, the temperature change of the texture was observed under a polarizing microscope. As a result, it was found that a ferroelectric liquid crystal was formed in the temperature range of 10° to 40° C., and its spontaneous polarization value was 20 nC/cm² at 25° C.

EXAMPLE 4 (COMPOSITION 3)

Using the liquid crystal compounds of samples 3, 4 and 8 and other SC* compounds and nematic liquid crystal compounds, a liquid crystal composition having the following components was prepared:

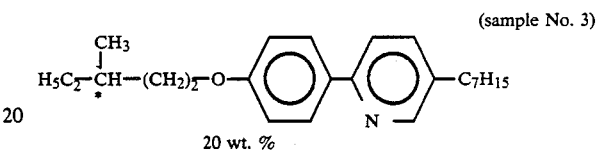
(sample No. 3)
20 wt. %

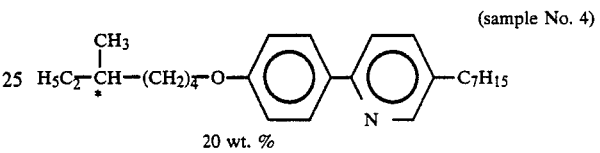
(sample No. 4)
20 wt. %

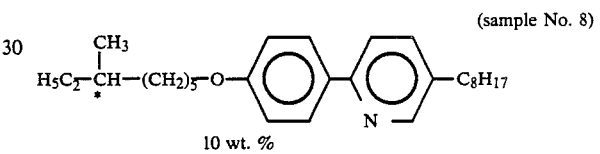
(sample No. 8)
10 wt. %

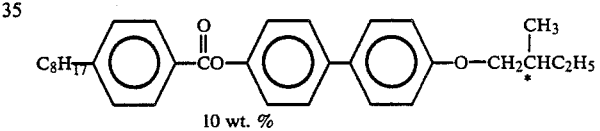
10 wt. %

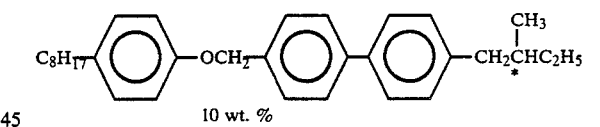
10 wt. %

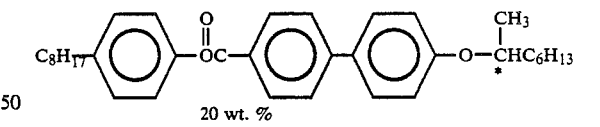
20 wt. %

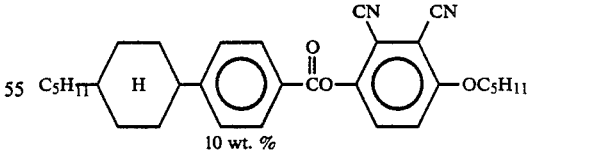
10 wt. %

The resulting composition was filled in the same cell 2 μm thick as in Example 3 and the resulting liquid crystal element was placed between two sheets of crossed polarizers. An electric field of 20 V was impressed and its intensity of transmitted light was observed. From the change in the intensity of transmitted light, the response time was sought to obtain a value of about 300 μsec at 25° C.

In addition, with the above liquid crystal composition, the temperature change of the texture was observed by means of a polarizing microscope. As a result, it was found that a ferroelectric liquid crystal was formed in the temperature range of 5° to 50° C., and its spontaneous polarization value was 13 nC/cm² at 25° C. and the tilt angle was 26°.

What we claim is:

1. A ferroelectric pyridine compound expressed by the formula

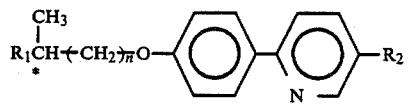 (I)

wherein n represents an integer of 1 to 8, $R_1$ represents an alkyl group of 2 to 18 carbon atoms, $R_2$ represents an alkyl group of 1 to 18 carbon atoms and the symbol * indicates that C having the symbol attached thereon is an optically active carbon atom.

2. A ferroelectric pyridine compound according to claim 1 wherein $R_1$ of said formula (I) is $C_2H_5$.

3. A ferroelectric pyridine compound according to claim 1 $R_1$ of said formula (I) is $C_6H_{13}$.

4. A ferroelectric pyridine compound according to claim 1 wherein $R_1$ of said formula (I) is $C_8H_{17}$.

5. A ferroelectric pyridine compound according to claim 1 wherein $R_2$ of said formula (I) represents an alkyl group of 6 to 10 carbon atoms.

6. A ferroelectric pyridine compound according to claim 1 wherein n of said formula (I) represents an integer of 3 to 5.

7. A chiral smectic liquid crystal composition comprising at least two components at least one of which is a ferroelectric pyridine compound expressed by the formula (I) as set forth in claim 1.

8. A light-switching element using a liquid crystal composition comprising at least two components at least one of which is a ferroelectric pyridine compound expressed by the formula (I) as set forth in claim 1 and exhibiting chiral smectic C phase.

* * * * *